United States Patent
Sengun

(10) Patent No.: US 9,597,068 B2
(45) Date of Patent: Mar. 21, 2017

(54) SELF-CINCHING SUTURE ANCHORS, SYSTEMS, AND METHODS

(71) Applicant: DePuy Mitek, LLC, Raynham, MA (US)

(72) Inventor: Mehmet Ziya Sengun, Canton, MA (US)

(73) Assignee: DePuy Mitek, LLC, Raynham, MA (US)

( * ) Notice: Subject to any disclaimer, the term of this patent is extended or adjusted under 35 U.S.C. 154(b) by 610 days.

(21) Appl. No.: 13/623,449

(22) Filed: Sep. 20, 2012

(65) Prior Publication Data

US 2014/0081325 A1    Mar. 20, 2014

(51) Int. Cl.
*A61B 17/04* (2006.01)

(52) U.S. Cl.
CPC .... *A61B 17/0401* (2013.01); *A61B 2017/044* (2013.01); *A61B 2017/0445* (2013.01); *A61B 2017/0448* (2013.01); *A61B 2017/0458* (2013.01); *A61B 2017/0461* (2013.01); *A61B 2017/0475* (2013.01)

(58) Field of Classification Search
CPC . A61B 17/04; A61B 17/0401; A61B 17/0469; A61B 2017/044; A61B 2017/0414; A61B 2017/0458; A61B 2017/0403; A61B 2017/0454; A61B 2017/0451; A61B 2017/0461; A61B 17/686; A61B 17/84; A61B 2017/0445; A61B 2017/0446; A61B 2017/0448; A61B 2017/0445; A61B 2017/0475
USPC ................................. 606/232, 300
See application file for complete search history.

(56) References Cited

U.S. PATENT DOCUMENTS 5,268,001 A * 12/1993 Nicholson et al. ........... 606/232
5,702,397 A   12/1997 Goble et al.
6,319,271 B1 * 11/2001 Schwartz et al. ............ 606/232
(Continued)

FOREIGN PATENT DOCUMENTS

CN     102596056 A    7/2012
WO   2006/037131 A2   4/2006
(Continued)

OTHER PUBLICATIONS

Central. Dictionary.com. Dictionary.com Unabridged. Random Hous, Inc. http://dictionary.reference.com/browse/central (accessed:Jan. 20, 2016).*
End. Dictionary.com. Dictionary.com Unabridged. Random House, Inc. http://www.dictionary.com/browse/end (accessed Aug. 1, 2016).*

(Continued)

*Primary Examiner* — Jonathan Miles
*Assistant Examiner* — Kankindi Rwego

(57) ABSTRACT

Various self-cinching suture anchors, self-cinching suture anchor systems, and methods of use are provided. In one exemplary embodiment, a suture anchor is provided that includes an outer member and an inner member configured to be received within the outer member. The inner and outer members can define a gap that allows a suture to be movably disposed within the outer member, e.g., within the gap, when the inner member is disposed within the outer member. The inner member can be configured to be secured within the outer member by a knot of the suture having a diameter greater than a width of the gap so as to fix the inner member within the outer member, while still allowing uni-directional tensioning of the suture.

20 Claims, 11 Drawing Sheets

(56) References Cited

U.S. PATENT DOCUMENTS

| | | | |
|---|---|---|---|
| 6,585,730 B1 | 7/2003 | Foerster | |
| 6,660,023 B2 | 12/2003 | McDevitt et al. | |
| 7,090,690 B2 | 8/2006 | Foerster et al. | |
| 8,114,128 B2 | 2/2012 | Cauldwell et al. | |
| 8,419,769 B2* | 4/2013 | Thal | A61B 17/0401 606/232 |
| 2004/0098050 A1* | 5/2004 | Foerster | A61B 17/0401 606/232 |
| 2009/0076544 A1 | 3/2009 | DiMatteo et al. | |
| 2009/0138042 A1* | 5/2009 | Thal | A61B 17/0401 606/232 |
| 2010/0016892 A1 | 1/2010 | Kaiser et al. | |
| 2010/0292732 A1* | 11/2010 | Hirotsuka et al. | 606/232 |

FOREIGN PATENT DOCUMENTS

| | | |
|---|---|---|
| WO | 2007/109769 A1 | 9/2007 |
| WO | 2012/024446 A2 | 2/2012 |

OTHER PUBLICATIONS

Align. Merriam-Webster.com. Accessed Aug. 5, 2016 http://www.merriam-webster.com/dictionary/align.*

[No Author Listed] "Mitek® Meniscal Repair System" brochure dated Mar. 1999.

[No Author Listed] "RapidLoc Meniscal Repair System Now With Top Hat" brochure dated Nov. 2002.

[No Author Listed] "RapidLoc® Meniscal Repair System" brochure dated Feb. 2008.

Barber et al. "Meniscal Repair With the RapidLoc Meniscal Repair Device," Arthroscopy: The Journal of Arthroscopic and related Surgery, vol. 22, No. 9 Sep. 2006, pp. 962-966.

U.S. Appl. No. 13/331,867 entitled "Knotless Instability Anchor" filed Dec. 20, 2011.

Extended European Search Report for Application No. 13185449.9 issued Dec. 16, 2013 (10 Pages).

Office Action and Search Report for Chinese Application No. 201310428279.9, dated Nov. 15, 2016.

* cited by examiner

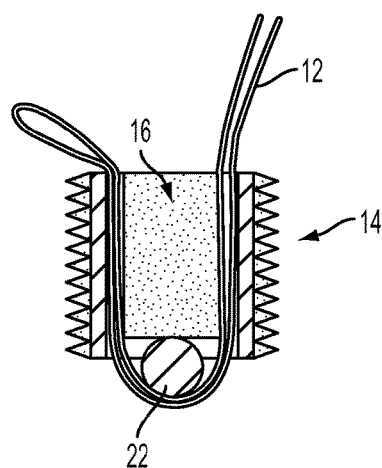
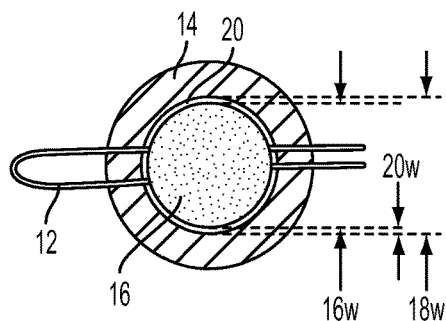
FIG. 5     FIG. 6
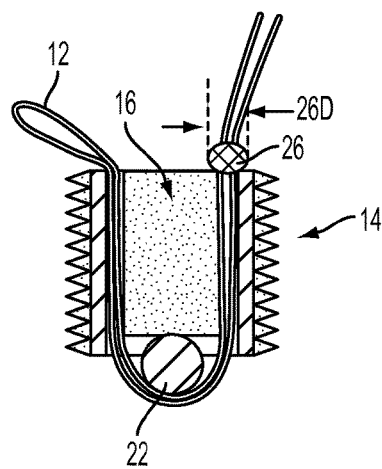
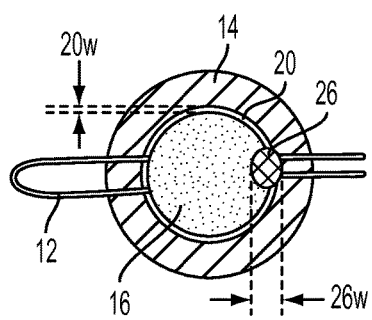
FIG. 7     FIG. 8

SELF-CINCHING SUTURE ANCHORS, SYSTEMS, AND METHODS

FIELD

The present disclosure relates generally to self-cinching suture anchors, self-cinching suture anchor systems, and methods for use.

BACKGROUND

The complete or partial detachment of ligaments, tendons, and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Numerous devices are currently available to re-attach soft tissue to bone. Examples of such currently-available devices include screws, staples, suture anchors, and tacks. In soft tissue re-attachment procedures utilizing screws, the detached soft tissue is typically moved back into its original position over the bone. The screw is then screwed through the soft tissue and into the bone, with the shank and head of the screw holding the soft tissue to the bone. Similarly, in soft tissue re-attachment procedures utilizing staples, the detached soft tissue is typically moved back into its original position over the bone. The staple is then driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. A suture anchor is then deployed in the hole using an appropriate installation tool. This effectively locks the suture, with soft tissue attached thereto.

While current suture anchors are effective in anchoring soft tissue to bone, one drawback with current devices is that the suture and soft tissue attached thereto can slip or otherwise move while the suture anchor is being driven into the bone. Once the suture anchor has been driven into bone, the suture and the soft tissue cannot be adjusted to adjust the position of the soft tissue relative to the bone because the driven suture anchor holds the suture and soft tissue in place. The soft tissue may therefore not be in an optimal position to facilitate healing.

Even if the suture and the soft tissue can be adjusted after the suture anchor has been driven into bone, tying the suture into a knot to secure the soft tissue in place relative to the bone can cause the soft tissue to slip from an optimal position. More particularly, surgeons typically tie suture ends using a surgical sliding knot such as the Tennessee Slider or Duncan Loop. After advancing the knot distally to tighten the loop, a number of additional half hitches or other knots are tied in an effort to secure the new location of the sliding knot. The additional knots are needed because a conventional sliding knot used in current repair constructs does not provide the necessary protection against loosening or slippage, especially when tension is placed primarily on the limbs of the loop. The generally accepted practice is to follow the sliding knot with at least three reversed half hitches on alternating posts of the suture. Before one or more half hitches or other knots can be added to the sliding knot, however, there exists a potential for the sliding knot to slip, that is, for the loop to enlarge as the tissue places tension on the loop. This has been referred to as "loop security" and can reportedly occur even in the hands of very experienced surgeons. Sometimes, even fully-tied knots may slip. In addition to this "loop security" problem, conventional knots can have an overall size that can be obstructive or intrusive, especially in tight joints, which may damage cartilage or other tissue by abrasion with the knot.

Accordingly, there remains a need for improved methods and devices for securing soft tissue to bone.

SUMMARY

The present invention generally provides self-cinching suture anchors, self-cinching suture anchor systems, and methods for use. In one aspect, a suture anchor is provided that includes an outer member having an inner lumen extending therethrough between proximal and distal ends thereof, and an inner member configured to be received within the inner lumen of the outer member. The outer member can have at least one bone-engaging surface feature formed on an outer surface thereof that is configured to engage bone. A suture receiving member can extend across the inner lumen of the outer member adjacent to the distal end, and the suture receiving member can be configured to receive a suture therearound. The suture receiving member can, in some embodiments, be in the form of a cross-bar extending between opposed inner sidewalls of the outer member. The inner member can have a maximum outer diameter that is less than a minimum inner diameter of the inner lumen of the outer member, and the inner member can have a length extending between proximal and distal ends thereof that is not greater than a length of the outer member extending between the proximal and distal ends of the outer member. When the inner member is fully disposed within the inner lumen of the outer member, a suture extending between the inner and outer members and around the suture receiving member can be configured to be freely slidable relative to the inner and outer members.

The inner member can vary in any number of ways. For example, the inner member can have a central lumen extending therethrough between proximal and distal ends thereof, and the inner lumen can be configured to have the suture extend therethrough. At least one of the inner member and the outer member can have at least one groove extending along an outer surface between proximal and distal ends thereof that can be configured to seat the suture therein.

In another aspect, a suture anchor system is provided that includes an outer member and an inner member removably disposable within the inner lumen of the outer member. The outer member can have an inner lumen extending therethrough between proximal and distal ends thereof and can have a suture receiving member adjacent to the distal end and configured to couple a suture to the outer member. In some embodiments, the outer member can have at least one bone-engaging surface feature formed on an outer surface thereof that is configured to engage bone. The inner and outer members can define a gap therebetween for slidably receiving a suture coupled to the suture receiving member. When the inner member is disposed within the inner lumen of the outer member such that a proximal end of the inner member is flush or sub-flush with a proximal end of the outer member, and when a suture is coupled to the suture receiving member, extends between the inner and outer members, and has a knot formed therein and positioned adjacent to the proximal ends of the inner and outer members, the suture can be freely slidable in only one direction within the gap relative to the inner and outer members. The inner member can be configured to be retained within the outer member solely by the knot when the suture is coupled to the inner and outer members.

The gap can be defined in a variety of ways. For example, the inner member can have an outer diameter that is less than a diameter of the inner lumen in the outer member such that the gap is formed by a space between the inner and outer members. For another example, the gap can be formed by a groove formed in one of the inner and outer members.

In yet another aspect, a surgical method is provided that includes threading a suture coupled to a soft tissue through an inner lumen of a suture anchor, around a suture receiving member located in a distal end portion of the suture anchor, and back through the inner lumen, the suture having first and second terminal ends that extend out of a proximal end of the suture anchor. The method can further include implanting the suture anchor in a bone hole, tensioning the first and second terminal ends of the suture to pull the suture around the suture receiving member and thereby pull the soft tissue toward the suture anchor, and forming a first knot with the first and second terminal ends of the suture such that the first knot is positioned adjacent to the proximal end of the suture anchor and to a proximal end of a plug disposed within the inner lumen. The suture can be threaded through the inner lumen of the suture anchor before implanting the suture anchor in the bone hole, e.g., as with a push-in anchor, or after implanting the suture anchor, e.g., as with a threaded anchor. In some embodiments, a portion of the suture can extend through a central lumen in the plug. The plug can allow free sliding movement of the suture within the inner lumen of the suture anchor. The first knot can have an outer diameter that prevents the first knot from passing between the suture anchor and the plug such that the first knot retains the plug within the suture anchor as tension is applied to the suture by the soft tissue. In some embodiments, after forming the first knot, a second knot can be formed adjacent to the first knot.

The method can also include inserting the plug into the inner lumen of the suture anchor to fully dispose the plug within the inner lumen of the suture anchor. In some embodiments, inserting the plug can include sliding the plug along the suture and into the inner lumen of the suture anchor.

The suture anchor can include a second suture anchor. Prior to implanting the second suture anchor in the bone hole, a first suture anchor can be implanted in a first bone hole, the suture extending around a suture receiving member formed in a distal end portion of the first suture anchor, through an inner lumen of the first suture anchor, and through the soft tissue. A knot can be formed in the suture adjacent to the soft tissue to secure the soft tissue against the first suture anchor.

BRIEF DESCRIPTION OF DRAWINGS

This invention will be more fully understood from the following detailed description taken in conjunction with the accompanying drawings, in which:

FIG. 5 is a side cross-sectional view of the outer member and the suture of FIG. 3 with the inner member of FIG. 1 disposed in the outer member;

FIG. 6 is a top view of the inner member, the outer member, and the suture of FIG. 5;

FIG. 7 is a side cross-sectional view of the outer member, the inner member, and the suture of FIG. 5 with a knot formed in the suture;

FIG. 8 is a top view of the inner member, the outer member, and the suture of FIG. 7;

DETAILED DESCRIPTION

Figure 1:
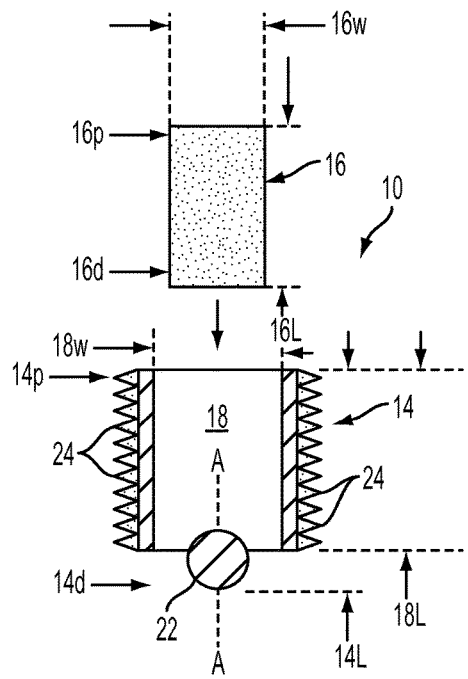
FIG. 1 is a side cross-sectional exploded view of one embodiment of a suture anchor including an inner member and an outer member.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various devices, systems, and methods are provided for securing soft tissue to bone. In general, various exemplary self-cinching suture anchors, self-cinching suture anchor systems, and methods of use are provided. In one exemplary embodiment, a suture anchor is provided that includes an outer member and an inner member configured to be received within the outer member. The inner member can be configured to be disposed within the outer member such that a gap exists between the inner and outer members. The inner and outer members can cooperate to allow a suture to slide freely between the outer and inner members, e.g., within the gap, when the inner member is disposed within the outer member. The inner member can be configured to be secured within the outer member by a knot of the suture having a diameter greater than a width of the gap so as to fix the inner member within the outer member. The outer member can include at least one bone-engaging surface feature on an exterior surface thereof and configured to engage bone so as to secure the outer member to bone and hence secure the inner member and the suture to the bone. In use, when the outer member is secured to bone, e.g., disposed within a bone hole, and the inner member and the suture are disposed within the outer member, the suture can be movable relative to the inner and outer members, which can allow a soft tissue attached to the suture to be optimally positioned relative to the bone even after the suture anchor has been secured to the bone. The anchor can therefore allow the soft tissue to be positioned relative to the bone both before and after the anchor has been driven into the bone, which can facilitate optimal positioning of the soft tissue relative to the bone for healing. Tension from the soft tissue coupled to the suture can self-cinch the knot of the suture, which can help prevent the knot from loosening, e.g., help provide "loop security," and thereby help hold the soft tissue in an optimal position relative to the bone during healing. The knot can be easily tied in a simple process, e.g., using a basic sliding knot or a basic half-hitch, and can be used alone without any additional knots, which can simplify the knot-tying and tissue-securing process and help ensure consistent results of the anchor from user to user. The configuration of the anchor is particularly advantageous as the tension applied to the tissue by the suture can be adjusted in one direction, e.g., tightened, while the knot secures the suture from sliding in the opposite direction. Accordingly, the system can provide uni-directional adjustment of the suture tension without the need to "lock" and "unlock" the anchor.

A person skilled in the art will appreciate that while methods, systems, and devices are disclosed herein for anchoring soft tissue to bone, the methods, systems, and devices can be used in a variety of other medical procedures for anchoring various objects to one another.

A person skilled in the art will appreciate that when an anchor disclosed herein is partially disposed in bone, e.g., within a bone hole or a bone tunnel, the anchor's distal end is disposed in the bone and the anchor's proximal end is proximal to a proximal surface of the bone. A person skilled in the art will also appreciate that when the anchor is fully disposed within the bone, the anchor's distal end is disposed in the bone and the anchor's proximal end is substantially flush or sub-flush with the proximal surface of the bone.

The anchors disclosed herein can be formed from a variety of materials. In an exemplary embodiment, material(s) forming an anchor can have physical properties that are sufficient to allow a driver to be used to drive the anchor into bone without damaging the anchor. The properties of the material(s) will depend on the particular configuration of the anchor. For non-limiting example, where the driver is inserted into the anchor's inner lumen, the inner lumen of the anchor can have a length that maximizes the torque strength of the anchor as well as the amount of surface contact between a driver and the anchor, thus allowing weaker materials, such as bioabsorbable and/or osteoconductive materials to be used. A person skilled in the art will appreciate that a variety of other materials, including polymers (e.g., polyetheretherketone (PEEK), polylactic Biocryl® Rapide available from DePuy Mitek of Raynham, Mass., acid (PLA), etc.) and metals (e.g., stainless steel, titanium, Nitinol, etc.), can be used to form the anchor. An outer member and an inner member of the anchor can each be formed of same material(s) or be formed of different material(s). In an exemplary embodiment, at least the inner member can be formed of substantially rigid material(s), which can help prevent the inner member from deforming or flexing. This can also help prevent a suture knot from slipping into a space defined between the inner and outer members, as discussed further below.

Figure 9:
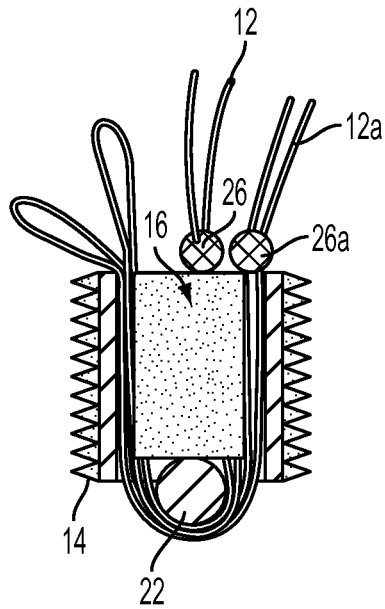
FIG. 9 is a side cross-sectional view of the outer member, the inner member, and the suture of FIG. 7 with a second suture having a second knot therein.
Figure 10:
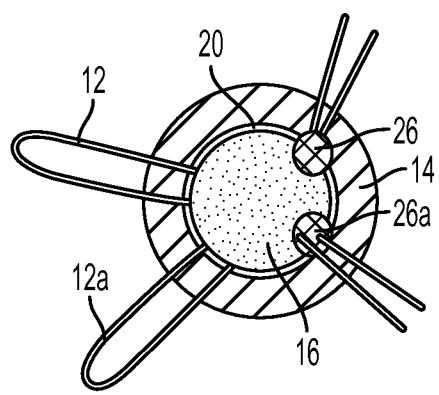
FIG. 10 is a top view of the inner member, the outer member, and the sutures of FIG. 9.

FIGS. 1-10 illustrate one exemplary embodiment of a suture anchor 10 configured to anchor soft tissue to bone. The anchor 10 can generally be configured to couple to at least one suture 12, and the anchor 10 can be configured to be disposed at least partially in bone, e.g., within a bone hole or a bone tunnel, so as to secure the at least one suture 12 to the bone and hence secure any material, e.g., a soft tissue, coupled to the at least one suture 12 to the bone. FIGS. 3-7 illustrate one suture 12 coupled to the anchor 10, and FIGS. 9 and 10 illustrate two sutures 12, 12a coupled to the anchor 10, but any number of sutures can be coupled to the anchor 10. Although the at least one suture 12 is shown as being coupled to the outer member 14 before the inner member 16 has been disposed within the outer member 14, in some embodiments, the inner member 16 can be disposed within an inner lumen 18 of the outer member before the at least one suture 12 is positioned within the inner lumen 18.

The anchor 10 can be elongate and can include an outer member 14 and an inner member 16, also referred to herein as a "plug," configured to mate to the outer member 14. The anchor 10 can thus include two discrete members 14, 16 configured to selectively mate together. In another embodiment, however, the inner member can be non-removably coupled to an outer member. The outer member 14 can have an inner lumen 18 extending therethrough between a proximal end 14p and a distal end 14d thereof. The inner member 16 can be configured to be at least partially disposed within the inner lumen 18 of the outer member 14. As in the illustrated embodiment, the inner member 16 can be configured to be fully disposed within the outer member 14. The inner member 16 can be disposed substantially flush or sub-flush within the outer member 14 so as to fully dispose the inner member 14 within the outer member 16 when the inner member 16 is fully distally advanced into the outer member 14. In other words, a proximal end 16p of the inner member 16 can be configured to be positioned substantially flush or sub-flush with a proximal end 14p of the outer member 14 when the distal end 16d of the inner member 16 is positioned within the outer member 14 and is proximal to or aligned with the outer member's distal end 14d. In the illustrated embodiment, as shown in FIGS. 5, 7, and 9, when the inner member 16 is fully distally advanced into the outer member 14, the inner member's proximal end 16p is configured to be substantially flush with the outer member's proximal end 14p when a distal end 16d of the inner member 16 is positioned within the outer member 14 at a location proximal to the outer member's distal end 14d.

Figure 2:
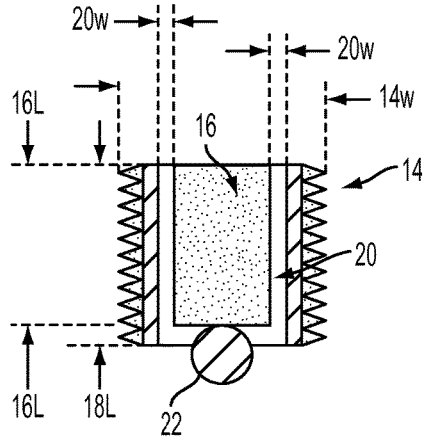
FIG. 2 is a side cross-sectional view of the suture anchor of FIG. 1 with the inner member disposed in the outer member.

As discussed further below, the inner member 16 can have a size and shape that allows a gap 20 to be formed between the inner member 16 and the outer member 14 even when the inner member 16 is fully distally advanced into the inner lumen 18, as shown in FIGS. 2 and 5. The outer and inner members 14, 16 can therefore cooperate to define the gap 20, also referred to herein as a "space," therebetween when the inner member 16 is disposed within the outer member 14. In one embodiment, the gap 20 can be defined by an outer surface of the inner member 16 and an inner surface of the outer member 14, and the gap 20 can extend longitudinally through the inner lumen 18 of the outer member 14. In another embodiment, the gap can be formed by grooves, channels, or other features in the inner and/or outer member that create a space for a suture to slide freely relative to the inner and outer members. As also discussed further below, the gap 20 can have a maximum width 20w greater than a maximum diameter 12D of the at least one suture 12, which can allow the at least one suture 12 to be freely movable within the gap 20, e.g., longitudinally and laterally slidable in the gap 20 relative to the outer and inner members 14, 16. In an exemplary embodiment, the maximum width 20w of the gap 20 can be greater than twice the maximum diameter 12D of the at least one suture 12 so as to allow at least two lengths of the suture 12 to extend through the gap 20 on opposite sides of the inner member 16, as shown in FIGS. 5-10, which can allow the at least one suture 12 to be folded. A folded suture can facilitate securing of the suture to soft tissue, as discussed further below.

The outer member 14 can have a variety of sizes, shapes, and configurations. The outer member 14 can be configured to be implanted within bone, such as within a bone hole, e.g., a hole having one open end and one closed end, or within a bone tunnel, e.g., a tunnel having two open ends. In an exemplary embodiment, the outer member 14 has a size and shape that allows it to be fully engaged through the thickness of the cortical bone. As in the illustrated embodiment, the proximal end 14p of the outer member 14 can be head-free, as the cannulated configuration of the outer member 14 can allow a driver or other installation tool to be inserted into the inner lumen 18 to drive the outer member 14 into bone. In other embodiments, however, an outer member can include a head, flange, or other feature on a proximal end thereof for driving the anchor into bone and/or limiting the insertion depth of the anchor. Exemplary configurations of an outer member of a suture anchor include the following anchors, all commercially available from DePuy Mitek of Raynham, Mass.: HEALIX®, HEALIX PEEK®, and HEALIX BR®.

As indicated above, the outer member 14 can be in the form of an elongate body having the inner lumen 18 extending therethrough. A suture seating member 22 can extend across the inner lumen 18 for receiving a suture therearound. The inner lumen 18 can extend along a complete longitudinal length 14L of the outer member, as in the illustrated embodiment, such that the outer member 14 is cannulated. The outer member 14 being cannulated can facilitate passage of the at least one suture 12 through the inner lumen 18 and around the suture seating member 22. In another embodiment, the inner lumen of an anchor's outer member can extend along a partial longitudinal length of the outer member.

The suture receiving member 22 can have a variety of sizes, shapes, and configurations. Generally, the suture receiving member 22 can be configured to receive, seat, or engage the at least one suture 12 extending at least partially through the inner lumen 18 so as to help securely couple the at least one suture 12 to the outer member 14. The suture receiving member 22, also referred to herein as a "cross bar," a "suture seating member," can be disposed within the inner lumen 18 adjacent to the distal end 14d of the outer member 14. Because the distal end 14d of the outer member 14 can define a distal end of the anchor 10, as shown in FIGS. 2, 5, 7, and 9, the suture receiving member 22 can thus be disposed adjacent to a distal end of the anchor 10. In another embodiment, a suture receiving member can be located proximal to a distal end of an anchor, e.g., proximal to a distal end of an outer member of the anchor.

Figure 4:
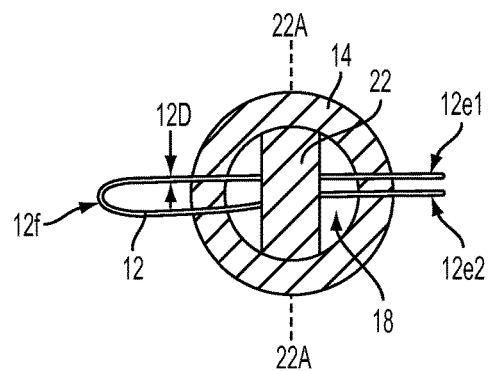
FIG. 4 is a top view of the suture anchor and the suture of FIG. 3.

The suture receiving member 22 can be configured to engage one or more sutures, e.g., the at least one suture 12, that extend through the inner lumen 18 of the outer member 14. As shown in the illustrated embodiment, the suture receiving member 22 can be in the form of a post that extends transversely across the inner lumen 18 and between opposed inner sidewalls of the outer member 14. An angular orientation of the suture receiving member 22 relative to a longitudinal axis A of the inner lumen 18 can vary, but in an exemplary embodiment, a longitudinal axis 22A of the suture receiving member 22 extends substantially perpendicular to the longitudinal axis A of the inner lumen 18, as shown in FIGS. 1 and 4. The suture receiving member 22 has a cylindrical shape and a circular cross-sectional shape in the illustrated embodiment, but the suture receiving member can have other shapes, e.g., hourglass-shaped, etc., and can have other cross-sectional shapes, e.g., ovular, hexagonal, etc. In an exemplary embodiment, at least a distal surface of the suture receiving member 22 can be curved or rounded, which can facilitate smooth sliding of the at least one suture 12 therearound.

The suture receiving member 22 can be integrally formed with the outer member 14, e.g., the outer member 14 and the suture receiving member 22 be molded as a single unit or formed from a single piece of material, or the suture receiving member 22 can be a discrete element fixedly or removably mated to the outer member 14, e.g., mated via snap fit. In an exemplary embodiment, the suture receiving member 22 can be configured to be non-movable, e.g., non-rotatable and non-slidable, relative to the outer member 14 whether the suture receiving member 22 is integrally formed with the outer member 14 or is a discrete element mated to the outer member 14. In another embodiment, the suture receiving member can be rotatable.

The suture receiving member can optionally include at least one groove (not shown) formed in an outer surface thereof. The at least one groove can be configured to seat one or more sutures, e.g., the at least one suture 12. The at least one groove can help predictably position the at least one suture 12 relative to the outer member 14 by seating the at least one suture 12 therein, which can help predictably position a soft tissue coupled to the at least one suture 12 relative to the outer member 14 and hence to bone in which the outer member 14 is disposed.

Various exemplary embodiments of suture receiving members are described in further detail in U.S. Pat. No. 8,114,128 entitled "Cannulated Suture Anchor" issued Feb. 14, 2012, and in U.S. Patent Publication No. 2009/0076544 entitled "Dual Thread Cannulated Suture Anchor" filed Sep. 14, 2007, which are hereby incorporated by reference in their entireties.

The outer member 14 can also include at least one bone-engaging surface feature 24 for engaging bone. The at least one bone-engaging surface feature 24 can have a variety of configurations, shapes, and sizes. In one embodiment, the at least one bone-engaging surface feature 24 can be formed on at least a portion of an external surface of the outer member 14, e.g., in a proximal portion of the outer member 14. A distal portion of the outer member 14 can be free of bone-engaging surface features. In other embodiments, the surface features can be formed along the entire length or along discrete portions of the outer member. While various surface features can be used, such as teeth, ridges, flanges, ribs, barbs, protrusions, etc., as in the illustrated exemplary embodiment, the outer member 14 can include at least one bone-engaging surface feature 24 in the form of one or more threads extending therearound. In the illustrated embodiment, the outer member 14 includes a single thread extending around the outer surface of the outer member 14 from the proximal end thereof to the distal end thereof, but an outer member can include a plurality of bone-engaging surface features, e.g., a plurality of threads, a plurality of ridges, etc. Various exemplary embodiments of bone-engaging surface features are described in further detail in previously mentioned U.S. Pat. No. 8,114,128 entitled "Cannulated Suture Anchor" issued Feb. 14, 2012, and U.S. Patent Publication No. 2009/0076544 entitled "Dual Thread Cannulated Suture Anchor" filed Sep. 14, 2007, and in U.S. patent application Ser. No. 13/331,867 entitled "Knotless Instability Anchor" filed Dec. 20, 2011, which is hereby incorporated by reference in its entirety.

Figure 11:
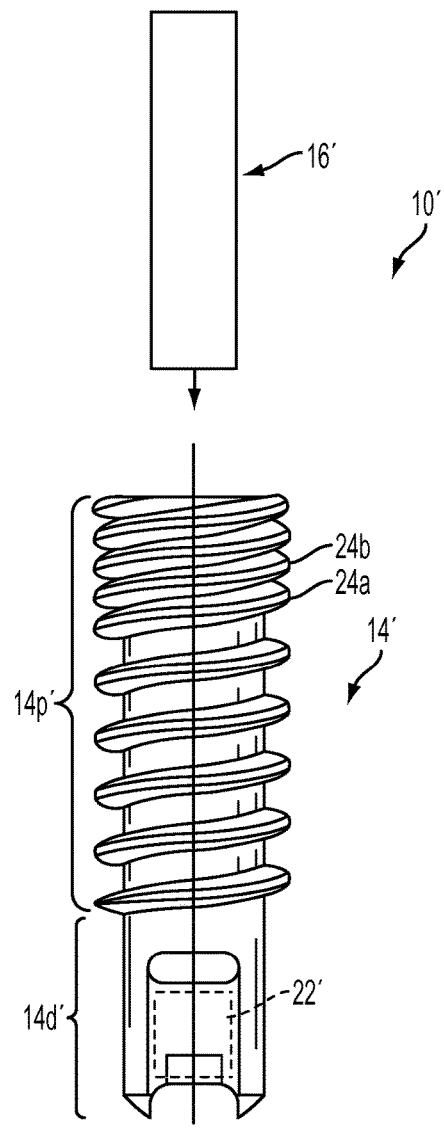
FIG. 11 is a side exploded view of another embodiment of a suture anchor including an inner member and an outer member.
Figure 12:
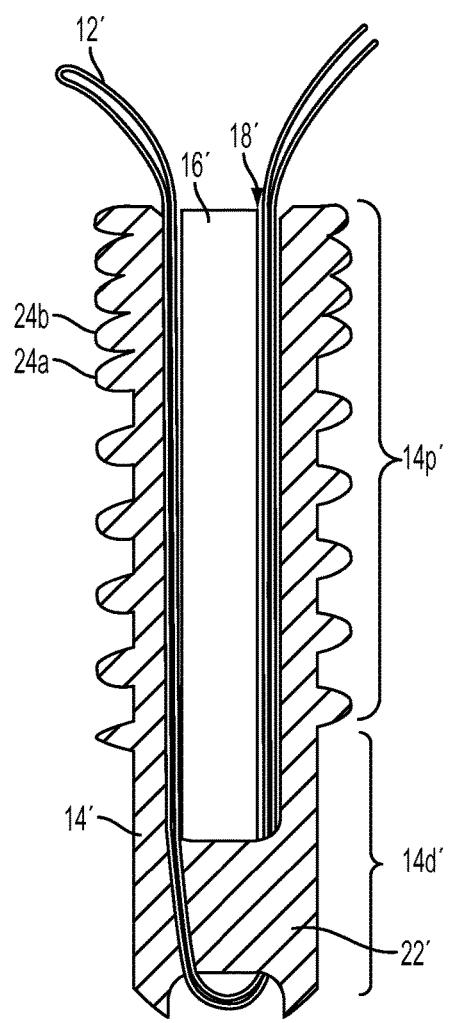
FIG. 12 is a side view of the suture anchor of FIG. 11 with the inner member disposed in the outer member and with a suture coupled to the inner and outer members.
Figure 13:
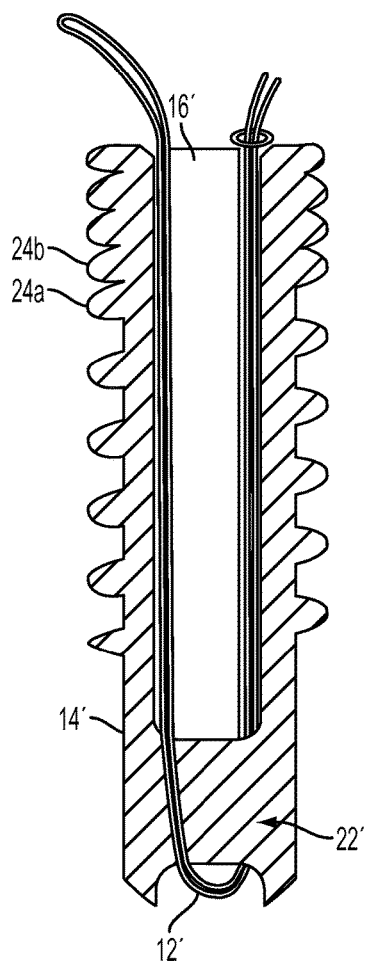
FIG. 13 is a side view of the inner member, the outer member, and the suture of FIG. 12 with a knot formed in the suture.

FIGS. 11-13 illustrate an embodiment of an anchor 10' including an outer member 14' having a plurality of bone-engaging surfaces features in the form of first and second threads 24a, 24b. FIGS. 11-13 also illustrate an inner member 16' configured to selectively mate to the outer member 14' and be received within an inner lumen 18' thereof. These figures also illustrate at least one suture 12' configured to couple to the outer and inner members 14', 16'. The anchor 10' can generally be configured and used similar to other anchors disclosed herein. The first and second threads 24a, 24b extend around the outer member 14' in a proximal portion 14p' of the outer member 14' such that the outer member 14' has a threaded proximal portion 14p' and a non-threaded distal portion 14d'. The first thread 24a originates at a proximal end of the outer member 14' and it terminates just proximal to a suture receiving member 22' of the outer member 14'. The suture receiving member 22' in this illustrated embodiment is located proximal to a distal end of the anchor 10', e.g., proximal to a distal end of the outer member 14'. The second thread 24b can extend between the first thread 24a. The second thread 24b can extend over only a portion of the outer member 14', or over an entire longitudinal length of the outer member 14'. As shown in FIGS. 11-13, the second thread 24b can extend along only a proximal-most portion of the outer member 14', and the second thread 24b can terminate proximal to the first thread 24a. As a result, the threaded proximal portion 14p' of the outer member 14' can include a dual threaded proximal region and a single threaded distal region. Various embodiments of outer members including a plurality of bone-engaging surface features are described in further detail in previously mentioned U.S. Patent Publication No. 2009/0076544 entitled "Dual Thread Cannulated Suture Anchor" filed Sep. 14, 2007.

Referring again to the embodiment of FIGS. 1-10, as shown in FIGS. 1 and 2, the outer member 14 can have a longitudinal length 14L that is equal to or greater than a longitudinal length 16L of the inner member 16, which can allow the inner member 16 to be fully disposed within the outer member 14. A longitudinal length 18L of the inner lumen 18 of the outer member 14 can thus also be equal to or greater than the inner member's longitudinal length 16L. As shown in FIGS. 1 and 6, a maximum width 18w of the outer member's inner lumen 18 can be greater than a maximum width 16w of the inner member 16, which can allow the inner member 16 to be loosely disposed within the inner lumen 18 and can create the gap 20 therebetween. Because the inner lumen 18 in the illustrated embodiment has a cylindrical shape and a circular cross-sectional shape, the maximum width 18w of the inner lumen 18 equals a diameter of the inner lumen's circular cross-sectional shape. Similarly, because the inner member 16 in the illustrated embodiment has a cylindrical shape and a circular cross-sectional shape, the maximum width 16w of the inner member 16 equals a diameter of the inner member's circular cross-sectional shape. Although the inner lumen 18 and the inner member 16 have the same shapes, e.g., cylindrical, and the same cross-sectional shapes, e.g., circular, in the illustrated embodiment, the inner lumen 18 and the inner member 16 can have different shapes and different cross-sectional shapes, same or different from one another. The inner lumen 18 and/or the inner member 16 can have different cross-sectional shapes along longitudinal lengths thereof and/or can have different diameters along longitudinal lengths thereof, e.g., the inner member 16 can have a truncated cone shape, a spherical shape, etc. In other words, the inner member 16 and/or the inner lumen 18 can have a variable cross-sectional shape along a longitudinal length thereof, e.g., does not need to have a constant cross-section along its length. The inner member 16 can have, e.g., a pointed or bullet-shaped distal tip and a proximal end having a size and shape adequate to form the gap 20 between the outer and inner members 14, 16 so as to allow securement of the inner member 16 within the outer member 14 using at least one knot, as discussed further below. The inner member 16 having such a pointed or bullet-shaped distal tip can make it easier to insert the inner member 16 into the inner lumen 18 of the outer member 14.

Figure 14:
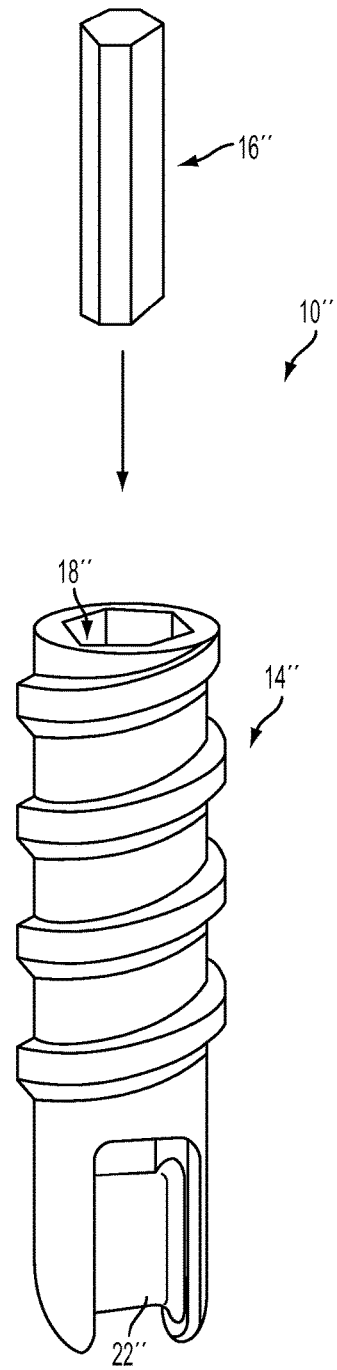
FIG. 14 is a side exploded view of yet another embodiment of a suture anchor including an inner member and an outer member.

FIG. 14 illustrates another embodiment of an anchor 10" including an inner member 16" having a hexagonal cross-sectional shape and an outer member 14" having an inner lumen 18" with a hexagonal cross-sectional shape. A suture receiving member 22" in this illustrated embodiment is located proximal to a distal end of the anchor 10", e.g., proximal to a distal end of the outer member 14". The anchor 10" can generally be configured and used similar to other anchors disclosed herein. The outer member 14" and various other embodiments of outer members are described in further detail in previously mentioned U.S. Pat. No. 8,114,128 entitled "Cannulated Suture Anchor" issued Feb. 14, 2012.

Referring again to the embodiment of FIGS. 1-10, the inner member 16 can have a variety of sizes, shapes, and configurations. The inner member 16 can, as in the illustrated embodiment, have a cylindrical shape and a circular cross-sectional shape. The inner member 16 can be substantially solid, as in the illustrated embodiment. A person skilled in the art will appreciate that the inner member 16 can be substantially solid despite including one or more material inconsistencies within manufacturing tolerances, such as by including small air bubbles. Alternatively, the inner member 16 can have one or more hollow portions, such as by being a hollow cylindrical member having closed ends, by being a hollow cylindrical member having one open end and one closed end, by having one or more hollow cavities contained within a member having closed ends, etc.

The inner member 16 can have a smooth outer surface without any surface features formed thereon, as in the illustrated embodiment. The smooth outer surface without any surface features can facilitate smooth slidable movement of the inner member 16 into the outer member's inner lumen 18 and/or can facilitate smooth slidable movement of the at least one suture 12 within the gap 20 defined by the outer and inner members 14, 16 when the inner member 16 is disposed within the outer member 14. In another embodiment, the inner member 16 can include at least one surface feature, e.g., a textured surface, a plurality of longitudinal ridges configured to longitudinally align one or more sutures along a longitudinal length of the inner member, etc.

Figure 15:
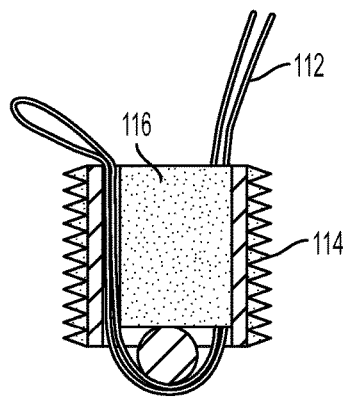
FIG. 15 is a side cross-sectional view of an embodiment of suture anchor including an outer member and an inner member, the inner member being disposed in the outer member and having a groove formed therein, and a suture being coupled to the inner and outer members and seated in the groove.
Figure 16:
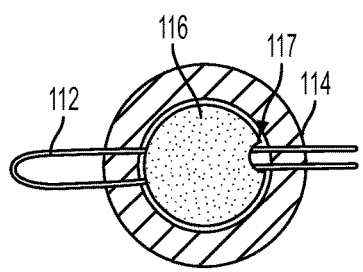
FIG. 16 is a top view of the inner member, the outer member, and the suture of FIG. 15.
Figure 17:
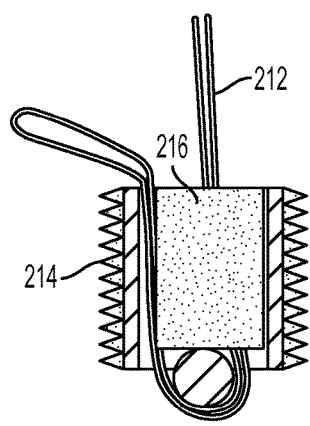
FIG. 17 is a side cross-sectional view of an embodiment of suture anchor including an outer member and an inner member, the inner member being disposed in the outer member and having a slot formed therein, and a suture being coupled to the inner and outer members and seated in the slot.
Figure 18:
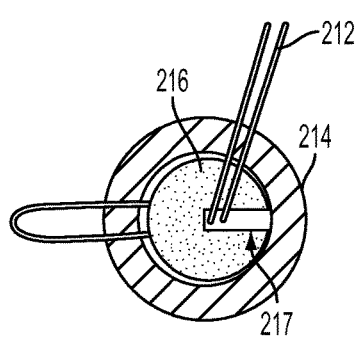
FIG. 18 is a top view of the inner member, the outer member, and the suture of FIG. 17.

In some embodiments, an inner member of a suture anchor can include at least one groove formed in an outer surface thereof that defines a gap between the inner and outer members. The at least one groove can have a variety of sizes, shapes, and configurations. The at least one groove can extend longitudinally along the inner member and can be configured to seat at least one suture therein. The at least one groove can facilitate predictable positioning of the at least one suture relative to an outer member in which the inner member including the at least one groove is disposed. FIGS. 15 and 16 illustrate an exemplary embodiment of an inner member 116 having at least one groove 117 formed in an outer surface thereof configured to seat at least one suture 112 therein. The at least one groove 117 in this illustrated embodiment includes a single longitudinal channel formed in an outer surface of the inner member 116, although an inner member can include more than one groove formed therein. The longitudinal channel can have, e.g., a crescent or half-moon cross-sectional shape as in the illustrated embodiment, or the longitudinal channel can have another shape and/or another cross-sectional shape. The at least one groove 117 can allow for the at least one suture 112 coupled to the inner member 116 to be seated therein and extend from a predictable position longitudinally around a perimeter of the inner member 116 when the inner member 116 is disposed in an outer member 114, which can facilitate tensioning of the at least one suture 112 and/or of a soft tissue coupled to the at least one suture 112. FIGS. 17 and 18 illustrate another exemplary embodiment of an inner member 216 having at least one groove 217 in the form of a slot formed in an outer surface thereof and configured to seat at least one suture 212 therein. The at least one groove 217 in this illustrated embodiment includes a single slot formed in an outer surface of the inner member 216 and extending radially inward, although as mentioned above, an inner member can include more than one groove formed therein. The longitudinal channel can have a rectangular cross-sectional shape as in the illustrated embodiment, or the longitudinal channel can have another shape and/or another cross-sectional shape. The at least one groove 217 can allow for the at least one suture 212 coupled to the inner member 216 to be seated therein and extend from a predictable position longitudinally around a perimeter of the inner member 216 when the inner member 216 is disposed in an outer member 214, which can facilitate tensioning of the at least one suture 212 and/or of a soft tissue coupled to the at least one suture 212. In other embodiments, the inner member can include two grooves positioned on opposite longitudinal sides of the inner member.

Figure 19:
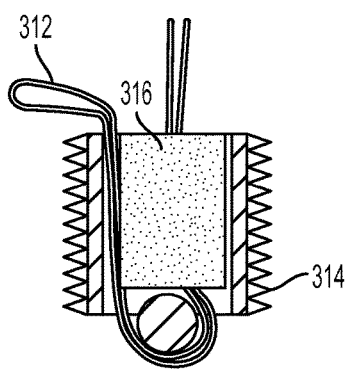
FIG. 19 is a side cross-sectional view of an embodiment of suture anchor including an outer member and an inner member, the inner member being disposed in the outer member and having an inner passageway extending therethrough, and a suture being coupled to the inner and outer members and extending through the inner passageway.
Figure 20:
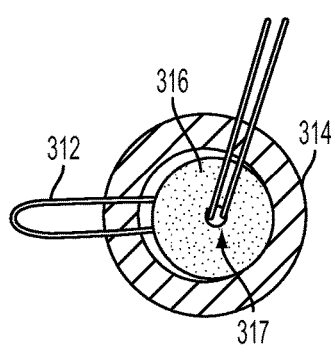
FIG. 20 is a top view of the inner member, the outer member, and the suture of FIG. 19.

In addition or in alternative to an inner member being configured to have at least one suture coupled to an outer surface thereof when the inner member is disposed within an outer member, the inner member can be configured to have at least one suture extend through an inner lumen thereof when the inner member is disposed within the outer member. FIGS. 19 and 20 illustrate an exemplary embodiment of an inner member 316 mateable to an outer member 314 and having an inner lumen 317 extending therethrough that can be configured to receive at least one suture 112 therein. The inner lumen 317 in this illustrated embodiment includes a single longitudinal inner lumen, but an inner member can include more than one inner lumen extending therethrough, such as two parallel lumens. The inner lumen 317 of the inner member 316 can have a cylindrical shape and a circular cross-sectional shape as in the illustrated embodiment, or the inner lumen 317 can have another shape and/or another cross-sectional shape.

Different cross-sectional shapes of an inner member can require different suture cinching techniques to be used, and in particular can dictate a size of a knot of a suture coupled to the anchor. By way of non-limiting example, the gap 20 between the outer and inner members 14, 16 of FIG. 2 can require use of a sliding knot, such as a bunt-line knot, with the at least one suture 12 extending through the gap 20, whereas a narrower space seating at least one suture, such as in the embodiment of FIGS. 17 and 18 including the at least one longitudinally-extending groove 217 in the form of a slot and in the embodiment of FIGS. 19 and 20 including a cannulated inner member 316, can allow for use of a cinching knot, such as a half-hitch knot, that is smaller than a sliding knot.

Referring again to the embodiment of FIGS. 1-10, the at least one suture 12 coupled to the anchor 10 can have a variety of sizes, shapes, and configurations, as will be appreciated by a person skilled in the art. As also will be appreciated by a person skilled in the art, the at least one suture 12 can be coupled to the anchor 10 in a variety of ways, e.g., by hand, by using a suture threading device, etc. In some embodiments, the at least one suture 12 can be pre-loaded within the inner lumen 18 of the outer member 14, e.g., packaged as a pre-loaded unit, which can speed usage of the anchor 10 in a surgical procedure.

Figure 3:
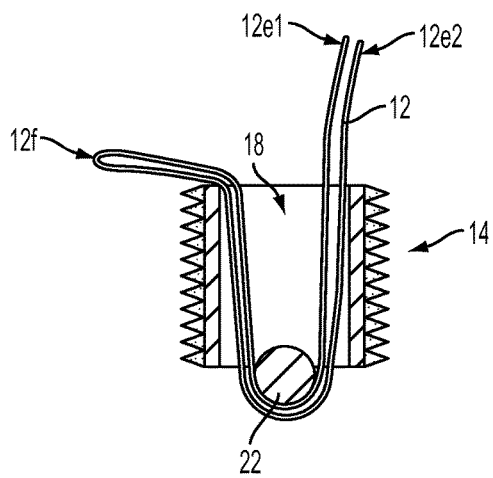
FIG. 3 is a side cross-sectional view of the outer member of FIG. 1 with a suture coupled thereto.

As shown in FIGS. 3 and 4, the at least one suture 12 can be configured to be positioned within the inner lumen 18 of the outer member 14 such that the suture 12 can be movable therein relative to the outer member 14, e.g., by sliding around the suture seating member 22. The at least one suture 12 can be positioned within the inner lumen 18 such that a first portion of the at least one suture 12 extends through the inner lumen 18 and out of the proximal end of the outer member 14, a second portion of the at least one suture 12 extends through the inner lumen 18 and out of the proximal end of the outer member 14, and a mid-portion of the at least one suture 12 located between the first and second portions of the at least one suture 12 is positioned around the suture seating member 22 at a location distal to the inner member 16. In an exemplary embodiment, as mentioned above, the at least one suture 12 can be positioned within the inner lumen 18 with the at least one suture 12 being folded. Such folding can allow terminal ends 12$e$1, 12$e$2 of the at least one suture 12 to define an end of the first portion of the at least one suture 12 extending out of the outer member 14 and a looped end or a folded point 12$f$ of the at least one suture 12 to define an end of the second portion of the at least one suture 12. The at least one suture 12 can be configured to be movable within the inner lumen 18, e.g., moving within the gap 20, even after the inner member 16 has been positioned within the inner lumen 18, as shown in FIGS. 5 and 6.

As discussed further below, when the inner member 16 is positioned within the inner lumen 18 and the at least one suture 12 is positioned within the gap 20 such that its terminal ends extend from the proximal end of the outer member 14, as shown in FIGS. 5 and 6, a knot 26 can be formed with the terminal ends 12$e$1, 12$e$2 of the at least one suture 12, as shown in FIGS. 7 and 8. The knot 26 can have a size that prevents the knot 26 from passing between the outer and inner members 14, 16. In an exemplary embodiment, the knot 26 can have an outer diameter 26D, shown in FIG. 7, that is greater than the maximum width 20$w$ of the gap 20. In other words, a minimum width 26$w$ of the knot 26, shown in FIG. 8, can be greater than the maximum width 20$w$ of the gap 20. Having a size greater than a size of the gap 20 can prevent the knot 26 from passing between the outer and inner members 14, 16, e.g., from passing into the gap 20, and can prevent the inner member 14 from being releasable from the outer member 16 (at least when the opposite end of the at least one suture 12 is coupled to the tissue and without first undoing the knot 26). A portion of the knot 26 may extend into the gap 20, e.g., be pulled therein due to a force exerted by a tissue attached to the folded end 12$f$ of the at least one suture 12, but the size of the knot 26 can prevent the knot 26 from fully passing into the gap 20 and can prevent the inner member 16 from being released from the outer member 14.

The knot 26 can be a sliding knot, or the knot 26 can be a simple knot such as a half-hitch. Because the knot 26 can be self-cinching, e.g., be tensioned from an opposite end 12$f$ of the at least one suture 12 attached to a tissue, both sliding knots and simple knots can be effective in securing the at least one suture 12 for effective anchor functionality.

Although only one knot 26 is shown formed with the at least one suture 12, a plurality of knots can be formed in the at least one suture 12. Each of the plurality of knots can have a size, same or different from a size of any of the other knots, that prevents the knot from passing between the outer and inner members 14, 16. Forming a plurality of knots with the at least one suture 12 can help ensure anchor functionality in the unlikely event of suture knot failure, e.g., knot unraveling, suture breakage, etc. In an embodiment that includes a plurality of sutures, such as shown in FIGS. 9 and 10, each knot 26, 26$a$ formed in the sutures 12, 12$a$ can have a size, same or different from one another, that prevents the knots 26, 26$a$ from passing between the outer and inner members 14, 16. Having multiple sutures 12, 12$a$ and hence also multiple knots 26, 26$b$ can help ensure anchor functionality in the unlikely event of suture failure. Additionally, as mentioned above, although only one knot 26, 26$a$ is shown formed with each of the sutures 12, 12$a$, each of the sutures 12, 12$a$ can have any number of knots formed therewith, same or different from each other. A knotting element can be used instead of a suture, as will be appreciated by a person skilled in the art.

In another embodiment, a suture anchor kit can be provided including one or more outer members and one or more inner members. In an exemplary embodiment, each of the inner members can be configured to be received within each of the outer members such that the inner members can be interchangeably used with the outer members. Each of the outer members can have a different size, different shape, and/or different configuration than the other outer members, and each of the inner members can have a different size, different shape, and/or different configuration than the other inner members. In this way, the outer member having the most appropriate size, shape, and configuration, and the inner member having the most appropriate size, shape, and configuration, can be selected for use in a particular surgical procedure with a particular patient, which can help a single kit accommodate different situations, such as different surgical procedures, different patient anatomies, various suture sizes, and various tissue sizes. The kit can optionally include one or more sutures configured to mate with the one or more inner members and the one or more outer members. As mentioned above, the suture(s) can be pre-loaded in the outer member(s), or the suture(s) can be loaded during or after the outer member is implanted. The sutures can have different sizes, different shapes, and/or different configurations from one another, which similar to that mentioned above, can allow suture(s) to be selected for use to accommodate different situations. The kit can include one or more additional surgical tools configured to be used with a suture anchor, e.g., one or more drivers, etc.

In use, as mentioned above, the suture anchors disclosed herein can be used in a minimally invasive surgical procedure for securing a soft tissue to bone. Generally, the patient can first be prepared for the surgery using standard techniques.

FIGS. 21-29 illustrate an exemplary embodiment of a surgical procedure for soft tissue repair. Although the procedure is illustrated with respect to the anchor 10 of FIGS. 1-8, any of the anchors disclosed herein can be similarly used. Also, although the procedure is illustrated with respect to a soft tissue repair, any of the suture anchors disclosed herein can be used to surgically repair various problems.

Figure 21:
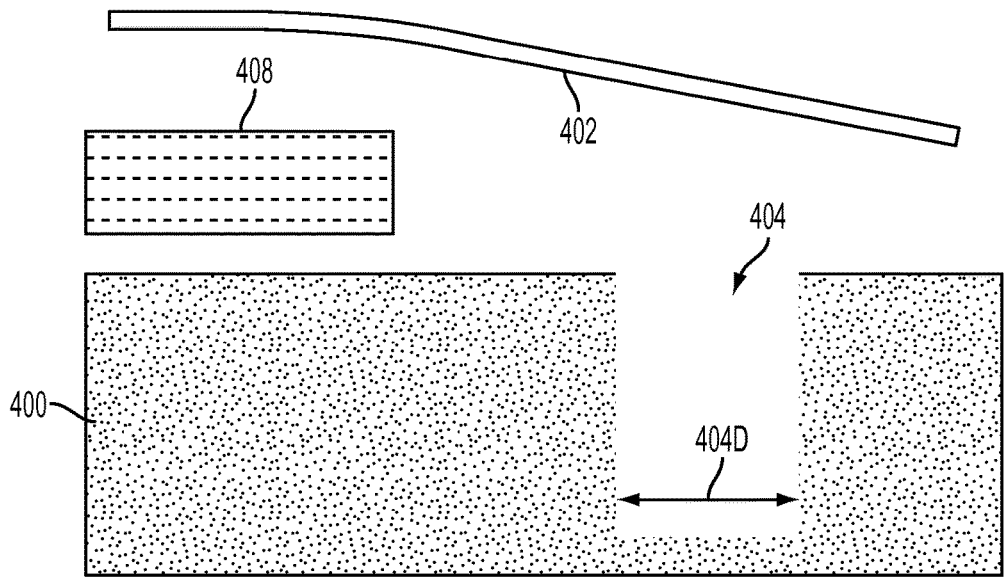
FIG. 21 is a side cross-sectional view of a bone underlying skin, a tissue being adjacent to the bone under the skin, and a bone hole being formed in the bone.

As shown in FIG. 21, a bone hole 404 can be formed in a patient's bone 400 underlying skin 402 of the patient. Although a bone hole 404 is shown in this embodiment, as mentioned above, anchors described herein can be used with bone tunnels. The bone hole 404 can be formed in a variety of ways, as will be appreciated by a person skilled in the art, such as by drilling. In an exemplary embodiment, the bone hole 404 can have a diameter 404D that is slightly less than a maximum outer width 14w of the outer member 14, shown in FIG. 2, which can facilitate engagement of the bone-engaging surface features 24 with the bone 400 and secure fit of the outer member 14 within the bone hole 404. Also in an exemplary embodiment, a longitudinal length 404L of the bone hole 404 can be substantially equal to or can be slightly greater than the longitudinal length 14L of the outer member 14, shown in FIG. 1, which can allow the outer member 14 to be fully disposed within the bone hole 404, e.g., with the proximal end of the outer member 14 being substantially flush or sub-flush with a proximal end of the bone hole 404, i.e., with a surface of the bone 400. The bone hole 404 can extend fully through cortical bone to allow the outer member 14 to be fully engaged through the thickness of the cortical bone. The bone hole 404 can also extend into cancellous bone underlying the cortical bone depending on the longitudinal length 14L of the outer member 14.

Figure 22:
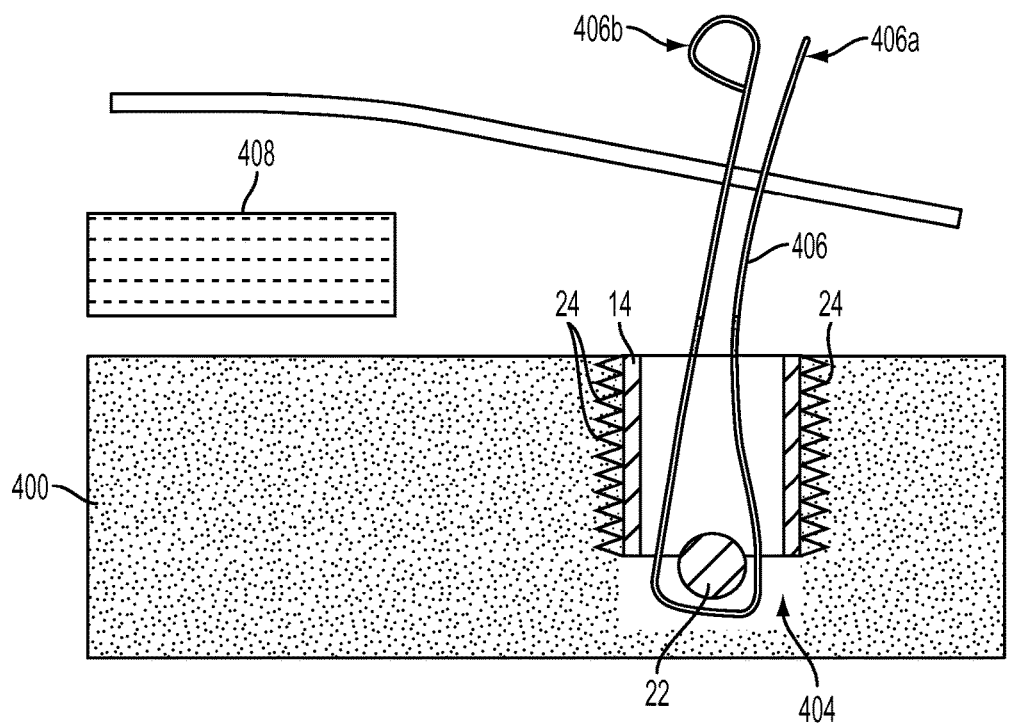
FIG. 22 is a side cross-sectional view of the bone, the skin, the tissue, and the outer member of FIG. 1 disposed in the bone hole of FIG. 21 and having a loading suture coupled thereto, the loading suture extending through the skin.

The outer member 14 can be inserted into the bone hole 404, as shown in FIG. 22. As will be appreciated by a person skilled in the art, the outer member 14 can be inserted into the bone hole 404 in a variety of ways, such as by inserting a distal tip of a driver into the inner lumen 18 through the proximal end of the outer member 14 and advancing the outer member 14 in a distal direction into the bone hole 404. The outer member 14 can be impacted into the bone hole 404 or driven therein using another technique, as will be appreciated by a person skilled in the art. As the outer member 14 advances distally into the bone hole 404, the bone-engaging surface feature 24 can engage the bone 400, e.g., thread into the bone 400 as the outer member 14 is rotated relative to the bone 400, which can help prevent removal of the outer member 14 from the bone hole 404.

Although the bone hole 404 is pre-formed in the bone 400 before the outer member 14 is advanced into the bone 400 in the illustrated embodiment, as will be appreciated by a person skilled in the art, the bone hole 404 can be partially formed in the bone 400 before an outer member is advanced therein. Alternatively, as will also be appreciated by a person skilled in the art, an outer member can be configured to form a bone hole as the outer member is advanced into the bone, such as by having a pointed distal tip that is substantially rigid.

The at least one suture 12 can be coupled to the outer member 14 before or after the outer member 14 is inserted into the bone hole 404. In an exemplary embodiment, the at least one suture 12 is coupled to the outer member 14 before the outer member 14 is inserted into the bone 400. If the at least one suture 12 is coupled to the outer member 14 before the outer member 14 is inserted into the bone 400, trailing ends of at least one suture 12, e.g., trailing ends of the first and second portions of the at least one suture 12, can extend externally along a driver used to advance the outer member 14 into the bone 400 and/or can extend through an inner lumen of the driver.

At least one loading suture 406 can be coupled to the outer member 14 to facilitate coupling of the at least one suture 12 to the outer member 14, as shown in FIGS. 22-25. The at least one loading suture 406 can be coupled to the outer member 14 before or after the outer member 14 is inserted into the bone hole 404. If the at least one loading suture 406 is coupled to the outer member 14 before the outer member 14 is inserted into the bone 400, trailing ends of the at least one loading suture 406 can extend externally along a driver used to advance the outer member 14 into the bone 400 and/or can extend through an inner lumen of the driver. In an exemplary embodiment, the at least one loading suture 406 is pre-loaded or factory-installed in the outer member 14, and the at least one suture 12 is threaded in the at least one loading suture 406 before the outer member 14 is implanted. The suture 12 can be coupled to outer member 14 using the loading suture 406 before or after insertion of the outer member 14 into the bone 400, e.g., if the outer member 14 is a push-in type member. If the outer member 14 is threaded into the bone 400, then the suture 12 can be coupled to the outer member 14 after insertion of the outer member 14 into the bone 400, which can help prevent the suture 12 from wrapping around the outer member 14 and/or the inserter tool used to drive the outer member 14 into the bone 400. Threading the outer member 14 into the bone 400 can give better fixation between the bone 400 and the anchor 10 than with a non-threaded outer member.

Whether the at least one loading suture 406 is coupled to the outer member 14 before or after the outer member 14 is inserted into the bone hole 404, the at least one loading suture 406 can be positioned within the inner lumen 18 similar to that discussed above for the at least one suture 12. As shown in FIG. 22, the at least one loading suture 406 can be coupled to the outer member 14 such that a first portion of the at least one loading suture 406 extends through the inner lumen 18 and out of the proximal end of the outer member 14, a second portion of the at least one loading suture 406 extends through the inner lumen 18 and out of the proximal end of the outer member 14, and a mid-portion of the at least one loading suture 406 located between the first and second portions of the at least one loading suture 406 is positioned around the suture seating member 22. A first end 406a of the at least one loading suture 406 can define an end of the first portion of the at least one loading suture 406 extending out of the outer member 14, and a second end 406b of the at least one loading suture 406 can define an end of the second portion of the at least one loading suture 406. The second end 406b can include a loading loop configured to facilitate coupling the at least one suture 12 to the outer member 14, although the first end 406a can also or alternatively include a loading loop. If the outer member 14 is implanted with the loading suture coupled thereto, the loading suture's second end 406b can be positioned relative to the bone 400 so that the loading suture's second end 406b is on a side of the bone hole 404 nearer a position where a soft tissue 408 is to be coupled to the bone 400, as shown in FIG. 22.

Figure 23:
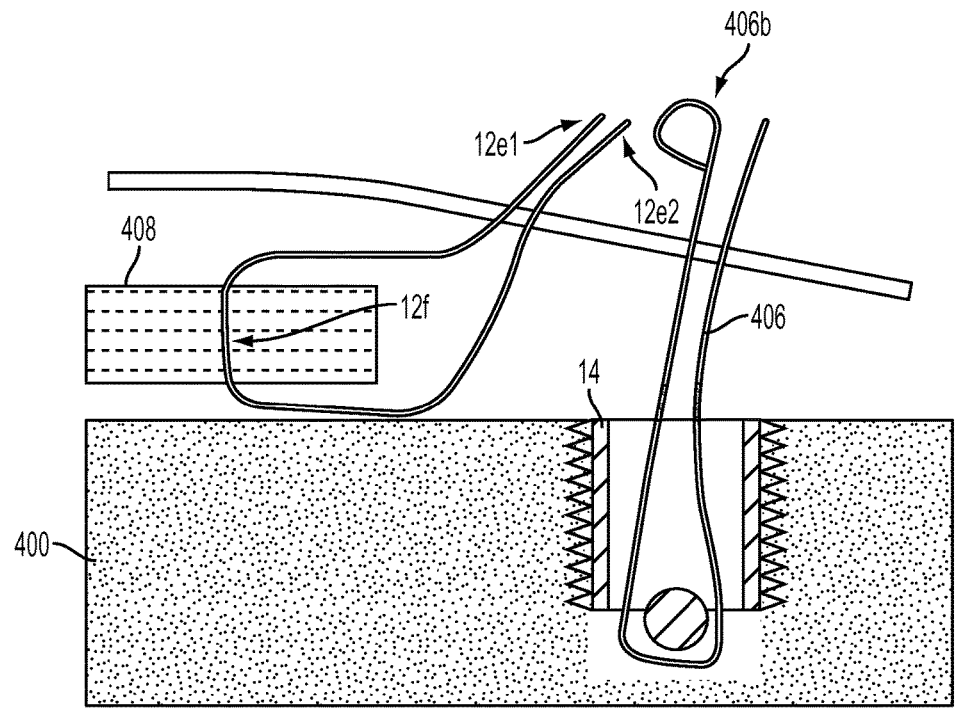
FIG. 23 is a side cross-sectional view of the bone, the skin, the tissue, the outer member, and the loading suture of FIG. 22 with the suture of FIG. 3 attached to the tissue of FIG. 22.

The at least one suture 12 can be coupled to the soft tissue 408 in any way, as will be appreciated by a person skilled in the art, such as by being passed through the soft tissue 408, e.g., using a needle. As shown in FIG. 23, the at least one suture 12 can be advanced through the soft tissue 408 such that one of the terminal ends 12e1 of the at least one suture 12 is positioned on one side of the soft tissue 408, the other of the terminal ends 12e2 of the at least one suture 12 is positioned on another, opposite side of the soft tissue 408, and the folded point 12f of the at least one suture 12 extends through or is positioned within the soft tissue 408.

Figure 24:
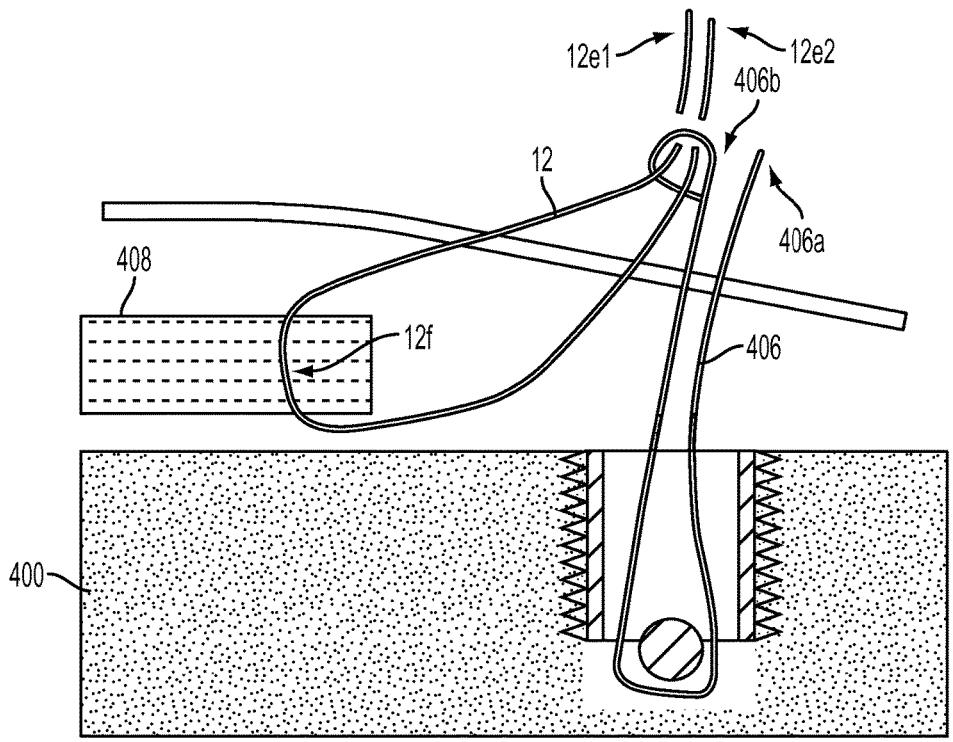
FIG. 24 is a side cross-sectional view of the bone, the skin, the tissue, the outer member, the suture, and the loading suture of FIG. 23 with the suture passed through the loading suture.
Figure 25:
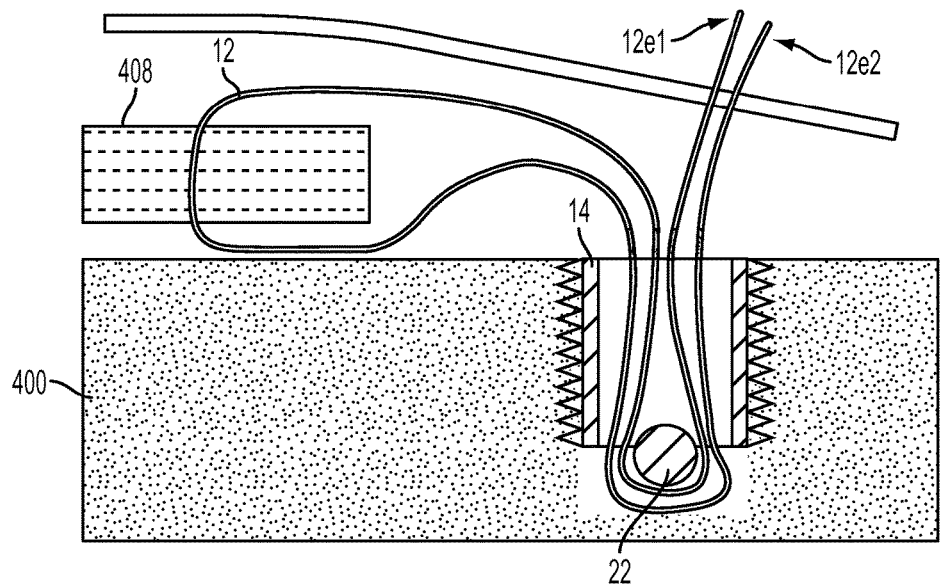
FIG. 25 is a side cross-sectional view of the bone, the skin, the tissue, the outer member, and the suture of FIG. 24 with the suture passed through the outer member and the skin.

The at least one suture 12 can be coupled to the at least one loading suture 406 to facilitate coupling of the at least one suture 12 to the outer member 14. In an exemplary embodiment, the at least one suture 12 and the at least one loading suture 406 can be coupled together by passing the terminal ends 12e1, 12e2 of the at least one suture 12 through the loading loop of the at least one loading suture 406, e.g., through the second end 406b, as shown in FIG. 24. The terminal ends 12e1, 12e2 of the at least one suture 12 can be so passed in any way, as will be appreciated by a person skilled in the art, e.g., by hand and/or by threading tool. As shown in FIG. 25, the at least one loading suture 406 having the at least one suture 12 coupled thereto, e.g., passed through the loading loop thereof, can be moved relative to the outer member 14 to advance the at least one suture 12 into the inner lumen 18. In an exemplary embodiment, the at least one loading suture 406 can be moved by pulling the first end 406a of the at least one loading suture 406 so as to pull the second end 406b of the at least one loading suture 406 and the at least one suture 12 into the inner lumen 18, around the suture seating member 22, and out of the inner lumen 18. Although the soft tissue 408 is shown as being coupled to the at least one suture 12 before the at least one suture 12 is coupled to the outer member 14, the soft tissue 408 can be coupled to the at least one suture 12 after the at least one suture 12 is coupled to the outer member 14, such as by tying the folded point 12f to the soft tissue 408 after the at least one suture 12 is coupled to the outer member 14.

Figure 26:
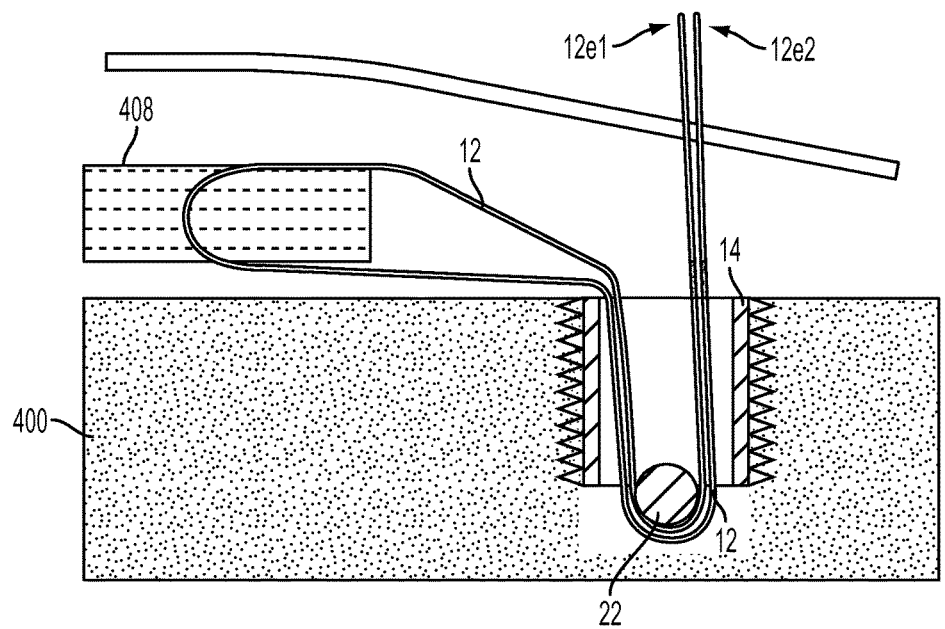
FIG. 26 is a side cross-sectional view of the bone, the skin, the tissue, the outer member, and the suture of FIG. 25 with the suture tensioned.

With the at least one suture 12 coupled to the outer member 14, and with the at least one suture 12 coupled to the soft tissue 408, as shown in FIG. 26, the at least one suture 12 can be tensioned relative to the bone 400 and the outer member 14, thereby tensioning the soft tissue 408 relative to the bone 400 and the outer member 14. The at least one suture 12 can be tensioned in any way, as will be appreciated by a person skilled in the art, e.g., by pulling the terminal ends 12e1, 12e2 simultaneously by hand and/or by tool.

Figure 27:
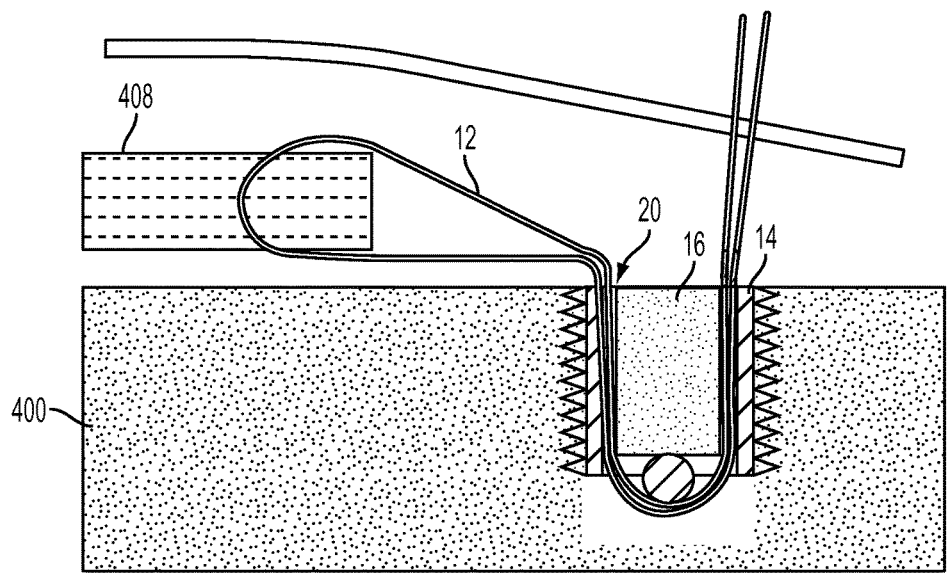
FIG. 27 is a side cross-sectional view of the bone, the skin, the tissue, the outer member, and the suture of FIG. 26 with the inner member of FIG. 1 disposed in the outer member and the suture extending between the inner and outer members.

The inner member 16 can be inserted into the inner lumen 18 of the outer member 14, as shown in FIG. 27, with the at least one suture 12 positioned in the gap 20 defined by the outer and inner members 14, 16. The inner member 16 can be inserted into the outer member 14 before the at least one suture 12 is tensioned, but tensioning the at least one suture 12 before inserting the inner member 16 into the outer member 14 can help prevent the inner member 16 from snagging on the at least one suture 12 and/or help prevent the at least one suture 12 from wrapping or tangling around the inner member 16 so as to hinder free movement of the at least one suture 12 within the gap 20. Also, the inner member 16 can be positioned in the outer member 14 with the at least one loading suture 406 before or after the outer member 14 is implanted.

Because the outer and inner members 14, 16 define the gap 20 therebetween when the inner member 16 is fully disposed therein, the at least one suture 12, and hence the soft tissue 408 attached thereto, can be tensioned after the inner member 16 has been inserted into the outer member 14, e.g., by sliding the at least one suture 12 through the gap 20 relative to the bone 400 and the outer and inner members 14, 16. The soft tissue 408 can thus be selectively tensioned and adjusted in position relative to the bone 400 and to the anchor 10 similar to a ratcheting system after the anchor 10 has been fully distally advanced into the bone hole 400. Advancement of the anchor 10 into the bone 400 and advancement of the at least one suture 12 through the anchor 10 will thus have no effect on position of the soft tissue 408 and the tension applied thereto by the at least one suture 12.

Figure 28:
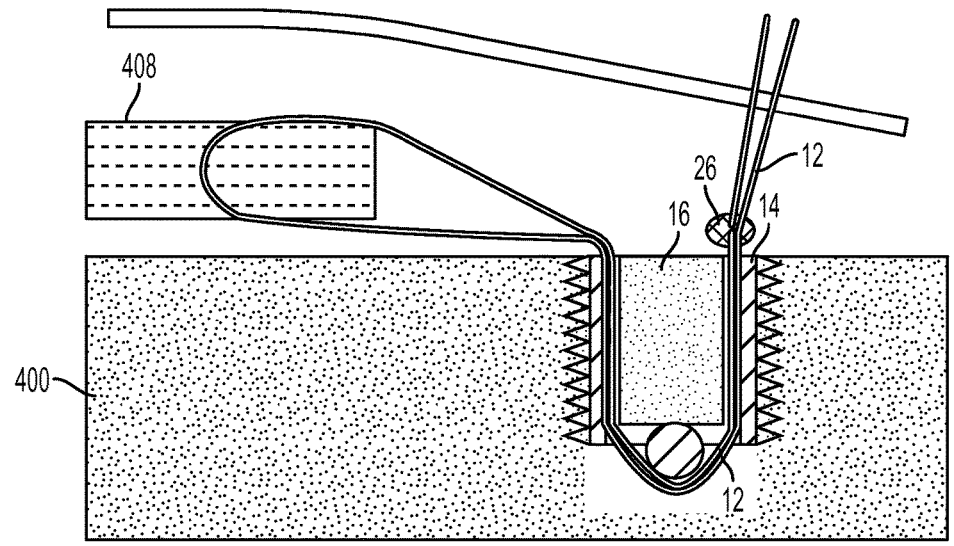
FIG. 28 is a side cross-sectional view of the bone, the skin, the tissue, the outer member, the inner member, and the suture of FIG. 26 with a knot formed in the suture.
Figure 29:
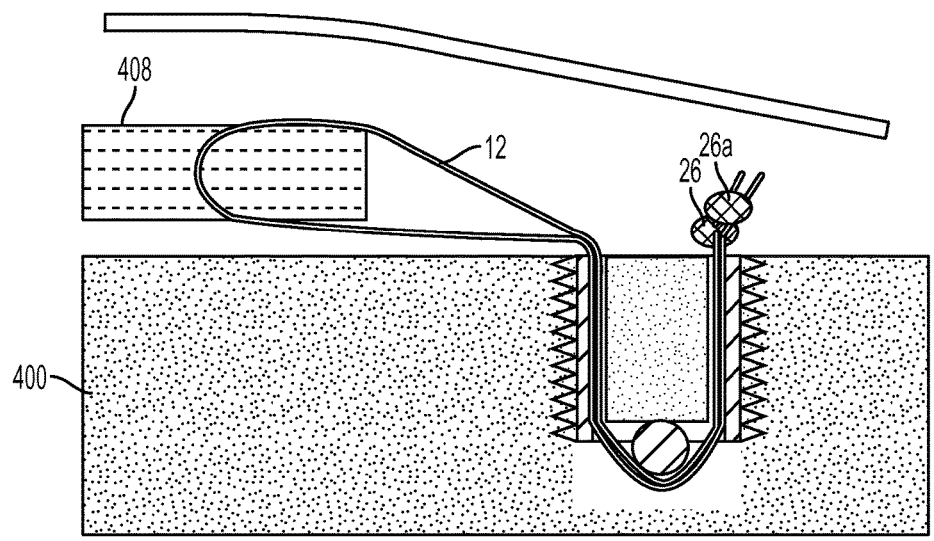
FIG. 29 is a side cross-sectional view of the bone, the skin, the tissue, the outer member, the inner member, and the suture of FIG. 26 with a second knot formed in the suture and with ends of the knot and second knot trimmed.

As shown in FIG. 28, a knot 26 can be formed in the at least one suture 12, thereby securing the soft tissue 408 in position relative to the bone 400 and to the anchor 10. The soft tissue 408 can provide a tension force to the at least one suture 12 so as to self-cinch the knot 26 and pull the knot 26 toward the anchor 10, which can help prevent the knot 26 from relaxing and can help prevent the movement of the at least one suture 12 relative to the bone 400, thereby holding the soft tissue 408 in place relative to the bone 400 for healing purposes. As explained above, the knot 26 can be made to have a size that prevents passage of the knot 26 through the gap 20 between the outer and inner members 14, 16. As a result, the soft tissue 408 will apply tension to the at least one suture 12 that pulls the knot 26 distally toward the distal end of the anchor, i.e., as a result of the at least one suture 12 extending around the suture receiving member 22. The knot 26 will this abut a proximal surface of the inner member 16, thereby pushing the inner member 16 distally into the outer member 14. The knot 26 will thereby retain the inner member 16 within the outer member 14 and simultaneously prevent slippage of the at least one suture 12 and movement of the soft tissue 408 away from the anchor 10. The at least one suture 12 can, however, be tensioned further to pull the soft tissue 408 toward the anchor 10. The knot 26 can be slid along the at least one suture 12 to increase the tension and/or one or more additional knots can be added to the at least one suture, as shown in FIG. 29. Accordingly, the anchor 10 allows for uni-directional movement of the at least one suture 12 to increase the tension applied to the soft tissue 408. The anchor 10 also provides simultaneous fixation of the inner member 16 within the outer member 14 without the need to "lock" and "unlock" the anchor 10. A person skilled in the art will appreciate that any one or more of the knots 26, 26a formed in the at least one suture 12 can optionally be loosened, readjusted, and/or removed by manually undoing the knot(s) 26, 26a, e.g., by picking on the knot(s) by hand and/or by tool, which can allow the soft tissue 408 to be readjusted again relative to the bone 400 and the anchor 10 if the soft tissue 408 is determined to not be in an optimal position relative to the bone 400, e.g., if too much tension is applied.

Figure 30:
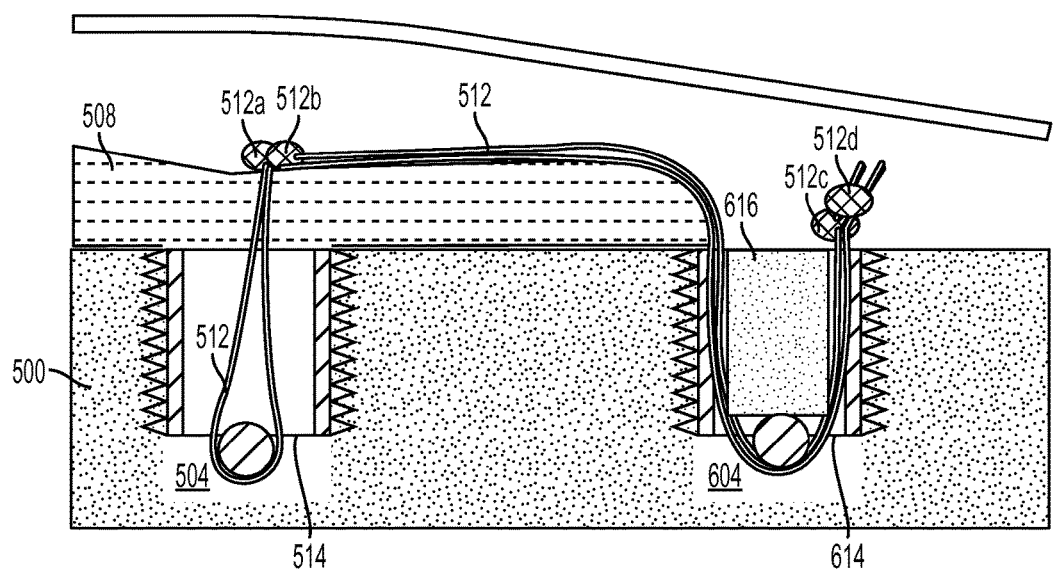
FIG. 30 is a side cross-sectional view of a bone underlying skin, a tissue adjacent to the bone under the skin, a suture passed through the tissue, first and second bone holes formed in the bone, a first outer member disposed in the first bone hole and having the suture extending therethrough, a second outer member disposed in the second bone hole and having the suture extending therethrough, and an inner member being disposed in the second outer member.

While FIGS. 21-29 illustrate a single-row soft tissue repair using a single anchor, the anchors disclosed herein can be used in multi-row soft tissue repair using multiple anchors. FIG. 30 illustrate an exemplary embodiment of a surgical procedure for double-row soft tissue repair using two anchors. Although the procedure is illustrated with respect to the anchor 10 of FIGS. 1-8, any of the anchors disclosed herein can be similarly used, and each of the anchors used in the procedure can be the same or different from one another. Also, although the procedure is illustrated with respect to a soft tissue repair, any of the suture anchors disclosed herein can be used to surgically repair various problems. The procedure of FIG. 30 can be generally the same as that discussed above regarding FIGS. 21-29, although only one of the outer members in the double-row soft tissue repair need have an inner member coupled thereto.

A first outer member 514, which can be configured and used similar to the outer member 14 of the anchor 10, can be advanced into a first bone hole 504 formed in bone 500. At least one suture 512, which can be configured and used similar to the at least one suture 12, can be advanced through the first outer member 514 before or after the first outer member 514 is advanced into the bone 400, and the at least one suture 512 can be coupled to a soft tissue 508 before or after the first outer member 514 is advanced into the bone 400. One or more knots 512a, 512b can be formed in the at least one suture 512 that faces a first surface of the soft tissue 508 that is opposite to a second side of the soft tissue 508 on the first outer member 514. An inner member does not need to be advanced into the first outer member 514 because the soft tissue 508 can be held in place by tension between the one or more knots 512a, 512b and a suture seating member 522 of the first outer member 514 around which the at least one suture 512 can be wrapped around.

Trailing ends of the at least one suture 512 can span over a portion of the soft tissue 508 and toward a second bone hole 604 formed in the bone 500, e.g., similar to a mattress stitch. A second outer member 614 can be positioned within the second bone hole 604, before or after the first outer member 514 is positioned within the first bone hole 504. The at least one suture 512 can be coupled to the second outer member 614, and an inner member 616 can be advanced into the second outer member 616 with the at least one suture 512 positioned in a gap defined between the outer and inner members 614, 616. One or more knots 512c, 512d can be formed in the at least one suture 512, thereby securing the soft tissue 508 in position relative to the bone 500 and to the second outer member 614 and its associated inner member 616. The one or more knots 512a, 512b associated with the first outer member 514 can provide a tension force to the at least one suture 512 so as to self-cinch the one or more knots 512c, 512d associated with the second outer member 614 and pull the one or more knots 512c, 512d toward the second outer member 614. The one or more knots 512c, 512d will thus also secure the inner member 616 within the second outer member 614. Although FIG. 30 illustrates the first tissue fixation point as being at the first outer member 514, the first tissue fixation point can otherwise be at the soft tissue 508, e.g., using fixation other than an outer member, such as another type of anchor. Additionally, although the one or more knots 512a, 512b are shown in the illustrated embodiment, the one or more knots 512a, 512b need not be present. The one or more knots 512c, 512d adjacent the second anchor including the outer and inner members 614, 616 can secure the soft tissue 508 in place.

In another embodiment of a multi-row soft tissue repair using multiple anchors, an anchor can be coupled to a plurality of sutures, each of the sutures trailing from different anchors. Using the anchor of FIGS. 9 and 10 as a non-limiting example, one of the sutures 12 can be coupled to a first outer member disposed in bone, or otherwise coupled to a first soft tissue fixation point, and the other of the sutures 12a can be coupled to a second outer member disposed in the bone, or otherwise coupled to a second soft tissue fixation point. Alternatively, each of the sutures 12, 12a can trail from a same outer member disposed in the bone, or otherwise can be coupled to a soft tissue fixation point. In another embodiment, one suture can be coupled to a plurality of anchors, e.g., like a mattress stitch.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A suture anchor, comprising:
   a cannulated outer member having an inner lumen extending therethrough between proximal and distal ends thereof, the outer member having at least one bone-engaging surface feature formed on an outer surface thereof and configured to engage bone, and the outer member having a suture receiving member extending transversely across an entire diameter of the inner lumen adjacent to the distal end, the suture receiving member being configured to receive a suture therearound; and
   an inner member configured to be received within the inner lumen of the outer member, the inner member having a maximum outer diameter that is less than a minimum inner diameter of the inner lumen of the outer member, and the inner member having a length extending between proximal and distal ends thereof that is not greater than a length of the outer member extending between the proximal and distal ends of the outer member;
   wherein when the inner member is fully disposed within the inner lumen of the outer member such that the distal end of the inner member abuts a proximal end of the suture receiving member and the proximal end of the inner member is flush with the proximal end of the outer member, a suture extending between the inner and outer members and around the suture receiving member is configured to be freely slidable relative to the inner and outer members.

2. The suture anchor of claim 1, wherein the inner member has a central lumen extending therethrough between proximal and distal ends thereof, the central lumen being configured to have the suture extend therethrough.

3. The suture anchor of claim 1, wherein at least one of the inner member and the outer member has at least one groove extending along a surface thereof between proximal and distal ends thereof, the groove being configured to seat the suture therein.

4. The suture anchor of claim 1, wherein the suture receiving member comprises a cross-bar extending between opposed inner sidewalls of the outer member.

5. The suture anchor of claim 1, wherein the suture is configured to be received in the inner lumen of the outer member such that when the inner member is fully disposed within the inner lumen of the outer member, the suture extends between the inner and outer members and around the suture receiving member and is freely slidable relative to the inner member and the outer member.

6. The suture anchor of claim 1, wherein a maximum width of the inner lumen is greater than a maximum width of the inner member.

7. The suture anchor of claim 1, wherein the suture receiving member is configured to prevent the inner member from being advanced into the inner lumen through the distal end of the outer member.

8. The suture anchor of claim 1, wherein the inner member being fully disposed within the inner lumen of the outer member includes the inner member being advanced as distally far as possible within the inner lumen.

9. The suture anchor of claim 1, wherein when the inner member is fully disposed within the inner lumen of the outer member, a space exists therebetween around a circumference of the inner member, the suture extending between the inner and outer members and around the suture receiving member being configured to be positioned within the space and be freely slidable therein relative to the inner and outer members.

10. The suture anchor of claim 1, wherein the suture receiving member is configured to receive the suture looped therearound such that first and second terminal ends of the suture extend out of the proximal end of the outer member.

11. The suture anchor of claim 1, wherein the inner lumen of the outer member has a first cross-sectional shape along a longitudinal length thereof and the inner member has a second cross-sectional shape along a longitudinal length thereof that is different from the first cross-sectional shape.

12. The suture anchor of claim 1, wherein a cross-sectional shape of the inner lumen of the outer member and a cross-sectional shape of the inner member are the same along respective longitudinal lengths thereof.

13. A suture anchor system, comprising:
a cannulated outer member having an inner lumen extending therethrough between proximal and distal ends thereof, the outer member having a suture receiving member adjacent to the distal end and configured to couple a suture to the outer member; and
an inner member removably disposable within the inner lumen of the outer member, the inner member being configured to be introduced into the inner lumen through the proximal end of the outer member and advanced in a distal direction within the inner lumen toward the suture receiving member until a proximal end of the inner member is flush with the proximal end of the outer member and a distal end of the inner member abuts a surface of the suture receiving member, outer members defining a gap therebetween for slidably receiving a suture coupled to the suture receiving member;
wherein, when the inner member is disposed within the inner lumen of the outer member such that the proximal end of the inner member is flush with the proximal end of the outer member and the distal end of the inner member abuts the surface of the suture receiving member, and when a suture is coupled to the suture receiving member, extends between the inner and outer members, and has a knot formed therein and positioned adjacent to the proximal ends of the inner and outer members, the suture is freely slidable in only one direction within the gap relative to the inner and outer members.

14. The system of claim 13, wherein the inner member is configured to be retained within the outer member by the knot when the suture is coupled to the inner and outer members.

15. The system of claim 13, wherein the outer member has at least one bone-engaging surface feature formed on an outer surface thereof that is configured to engage bone.

16. The system of claim 13, wherein the inner member has an outer diameter that is less than a diameter of the inner lumen in the outer member such that the gap is formed by a space between the inner and outer members.

17. The system of claim 13, wherein the gap is formed by a groove formed in one of the inner and outer members.

18. The suture anchor of claim 13, wherein when the suture is slid as far as possible in the only one direction within the gap, the inner member is configured to be retained within the outer member by the knot.

19. The suture anchor of claim 13, wherein the suture is freely slidable in the only one direction within the gap relative to the inner and outer members until the knot engages the proximal ends of the inner and outer members.

20. The suture anchor of claim 13, wherein the suture receiving member extends transversely across an entire diameter of the inner lumen.

* * * * *